United States Patent [19]

Borden

[11] Patent Number: 4,792,199

[45] Date of Patent: Dec. 20, 1988

[54] SYSTEM FOR DETECTION OF EXTREMELY SMALL PARTICLES IN A LOW PRESSURE ENVIRONMENT

[75] Inventor: Peter G. Borden, Palo Alto, Calif.

[73] Assignee: High Yield Technology, Mountain View, Calif.

[21] Appl. No.: 114,277

[22] Filed: Oct. 27, 1987

[51] Int. Cl.⁴ .............................................. G01N 1/00
[52] U.S. Cl. ..................................................... 356/37
[58] Field of Search .................. 73/865.5, 28; 356/335, 356/336, 37, 338, 337, 341, 343, 436, 437, 438, 340; 250/343, 435, 573, 574, 338 GA

[56] References Cited

U.S. PATENT DOCUMENTS

| | | | |
|---|---|---|---|
| 2,684,008 | 7/1954 | Vonnegut | 356/37 |
| 3,526,461 | 9/1970 | Lindahl et al. | 356/337 |
| 3,592,546 | 7/1971 | Gussman | 356/37 |
| 3,694,085 | 9/1972 | Rich | 356/37 |
| 3,890,046 | 6/1975 | Hart et al. | 356/37 |
| 4,477,187 | 10/1984 | Pettet et al. | 356/335 |
| 4,670,637 | 6/1987 | Morrison et al. | 356/335 |
| 4,696,571 | 9/1987 | Goldberg et al. | 250/574 |

Primary Examiner—Stewart J. Levy
Assistant Examiner—Robert R. Raevis
Attorney, Agent, or Firm—Nathan N. Kallman; Alan H. MacPherson; Paul J. Winters

[57] ABSTRACT

A system for detection of extremely small particles in a low pressure environment or vacuum includes a vapor column in which a diffusion oil is vaporized, a saturation column in which vaporized oil is cooled and supersaturated, and means for directing a low pressure gas into the saturation column. An optical detector senses the oil droplets that grow around extremely small particles which are introduced in the saturation column by the gas and fall past the detector.

8 Claims, 2 Drawing Sheets

SYSTEM FOR DETECTION OF EXTREMELY SMALL PARTICLES IN A LOW PRESSURE ENVIRONMENT

FIELD OF THE INVENTION

This invention relates to a system for detecting extremely small particles in a low pressure environment or a vacuum, particularly during semiconductor wafer fabrication.

BACKGROUND OF THE INVENTION

Semiconductor wafer fabrication processes are especially susceptible to yield loss due to particle contamination. Free particles landing on a wafer surface during processing can produce defects in patterns and deposited layers that result in device failure. A primary source of these free particles is the vacuum processing equipment that is used for process steps such as the deposition of dielectric and conduction layers, the plasma etching of patterns, the electron beam writing of fine patterns, ion implantation of dopants into the wafer surface, and the dry stripping of photoresist.

Such contaminant particles present in the processing equipment range in diameter from less than 100 angstroms to several microns. Typical sources include debris broken from wafers during handling, chemical reactions in the equipment, and the flaking of material from the walls of the equipment. Particles greater in size that one tenth of the smallest pattern geometry are generally of concern as they may produce defects in the wafers that are being fabricated. For example, a 1 megabit dynamic random access memory (DRAM) will use 1 micron lines, and 0.1 micron particles will be of concern, and a 16 megabit DRAM will use 0.5 micron lines, and 0.05 micron particles will be of concern.

The only known means available today to monitor such small particles in vacuum process equipment is to collect them on plates or wafers and scan the collection plates with a scanning electron microscope. This is a very tedious and time consuming procedure, is an off-line measurement, and requires expensive equipment. A real-time, automatic measurement is preferred because it is desirable to detect problems as they occur, so a solution can be effected before significant damage occurs to the wafers being processed.

Real-time techniques exist to monitor particles greater than 0.5 microns in diameter in vacuum, and to monitor extremely small particles much less than 0.5 microns in diameter in air. A real-time system for monitoring particles in vacuum systems is disclosed in co-pending U.S. patent application Ser. No. 07/041,795, entitled "A Compact Particle Flux Monitor", filed on behalf of P. Borden et al. and assigned to the same assignee. The particle flux monitor employs an optical system to create a net of light in space. As particles pass through this net, they scatter light to photodetectors. This technique is not applicable below 0.5 micron particles size because the particles become small compared to the light wavelength, and the scattering becomes too small to detect. Other techniques for monitoring small particles, such as the airborne particle counter and the condensation nucleation counter (CNC) are not applicable because they use suction to draw air laden with suspended particles into a measuring area. This suction cannot be applied to vacuum systems.

The CNC detects extremely small particles, as small as 0.01 microns in diameter. A description of this counter instrument is provided in the textbook by William C. Hinds, entitled "Aerosol Technology", published by John Wiley and Sons, 1982, see section 13.6. During operation, the instrument passes air through a saturation tube to saturate the air with alcohol vapors. The air is then chilled and is supersaturated thereby forcing the alcohol to condense onto particles suspended in the air, which act as nucleation sites. The particles grow to a size that allows them to be counted using normal light scattering techniques.

Prior art vacuum technology employs vapor booster pumps that use the principles of diffusion and ejection, as described in the textbook entitled "Vacuum Technology", by A. Roth, published by North-Holland Physics Publishing, Second Revised Edition, 1982, see section 5.3. Diffusion pumps operate by creating a flow of the vapors of special oils. Gas molecules are caught in this flow and are carried away, resulting in a pumping action. The vapor flow is supersaturated while retaining the pumping action. Very small particles trapped in this flow will act as nucleation sites for the oil vapors and quickly grow into droplets several microns in diameter. These large droplets can be detected using light scattering.

However the prior art technology and techniques do not provide a means for the detection of extremely small particles in a vacuum or low pressure environments.

SUMMARY OF THE INVENTION

An object of this invention is to provide a means to monitor extremely small particles in low pressure environments in real-time.

In accordance with this invention, a system for real-time detection of extremely small particles in a low pressure environment comprises a vapor column for generating liquid vapors, a saturation column wherein the vapors are cooled and supersaturated, a nozzle for ejecting the vapors from the vapor column into the saturation column, and an optical detector for counting droplets of the cooled and supersaturated vapors as the droplets fall through a beam of light.

DESCRIPTION OF THE DRAWING

The invention will be described in greater detail with reference to the drawing in which.

DETAILED DESCRIPTION OF THE INVENTION

Figure 1:
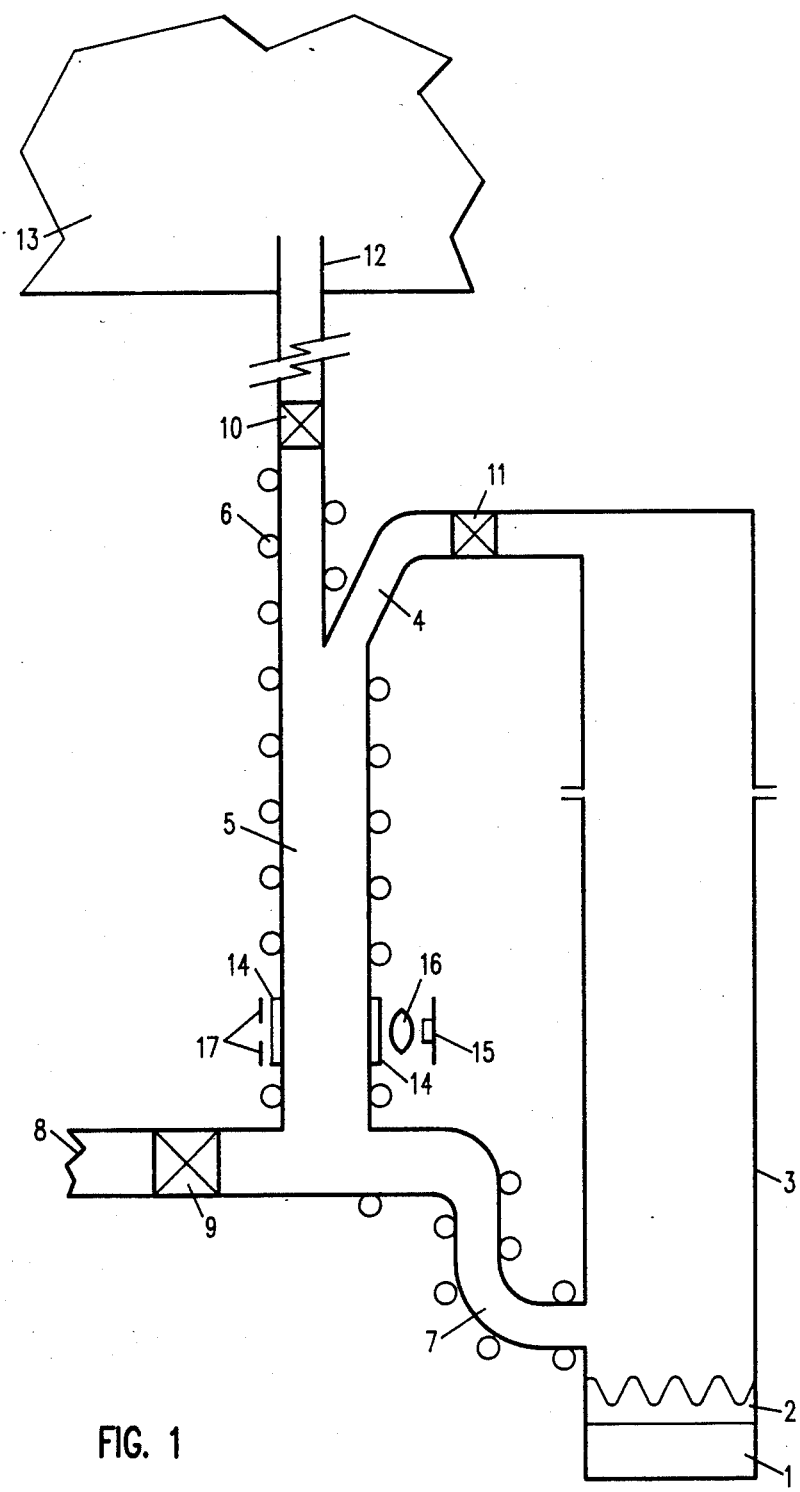
FIG. 1 is a schematic sectional diagram of a particle detector system, made in accordance with this invention.

With reference to FIG. 1, a system for detecting extremely small particles comprises a vapor column 3 having a reservoir 2 with an oil disposed at the bottom of the column 3. The oil is preferably Fomblin 425/9 diffusion oil, well known in the technology.

During operation, a heater 1 heats the oil to a temperature that will cause vaporization. The oil vapors rise in the vapor column 3 and are directed down through a nozzle 4 into a saturation column 5. The saturation column is made of a heat conductive material, such as copper or brass, and has water cooling tubes or a coil 6 soldered to its exterior. In this manner, the temperature of the saturation column or tube 5 can be made lower than the temperature of the vapor column 3, causing the oil vapors to supersaturate in the saturation column. The cool walls of the saturation column also allow the vapors to condense. The condensed oil returns to the oil reservoir 2 through an oil return conduit 7. The downward spray of the oil vapors out of nozzle 4 result in a pumping action in the saturation column 5.

A sample probe 12 fits into a vacuum chamber 13, for sampling a very low pressure gas. The low pressure gas is drawn with suspended particles by the pumping action into the saturation column 5. The cooling coil 6 extends up to the sample probe 12 to effectuate condensation of the oil vapors, so that they do not backflow into and contaminate the vacuum chamber 13.

A vacuum pump (not shown), such as a rotary vane pump, fits onto a diffusion pump nucleation counter (DPNC) at port 8. The connection of the pump to the DPNC is required because the background pressure of the DPNC must be lowered to about 100 milliTorr to function properly. At higher pressures, there is a risk of burning the pump oil, and the pumping action loses effectiveness. Valve 10 serves to isolate the DPNC from the vacuum chamber 13, so that the vacuum chamber can be vented to atmospheric pressure. Valve 9 controls the rate at which the rotary vane pump removes oil vapors, and valve 11 controls the rate at which vapors are ejected through the nozzle 4.

The optical system used to detect the oil droplets as they fall in the saturation tube 5 is located near the bottom of the saturation tube. A laser beam shines into the tube through window 14A. A collimated beam of light is formed with laser source 15 and lens 16. The laser 15 is typically an AlGaAs laser diode with 10 milliwatts power at a wavelength of 780 nanometers by way of example. Photocells 17 are mounted on the opposite window 14B displaced substantially symmetrically from the optical axis of the windows. The windows are slightly recessed into the tube 5 so that the windows will not be coated by oil running down the inner wall of the saturation tube. The photocells collect light scattered by droplets that pass through the laser beam. The beam can typically be oval in shape, about 0.5 cm wide and 0.3 cm thick. The DPNC can be used on vacuum systems wherein the vacuum chamber is operating down to about 10E-6 Torr. Below this pressure, the diffusion pump principle ceases to be effective, and small amounts of oil vapor may backstream into the vacuum chamber.

Figure 2:
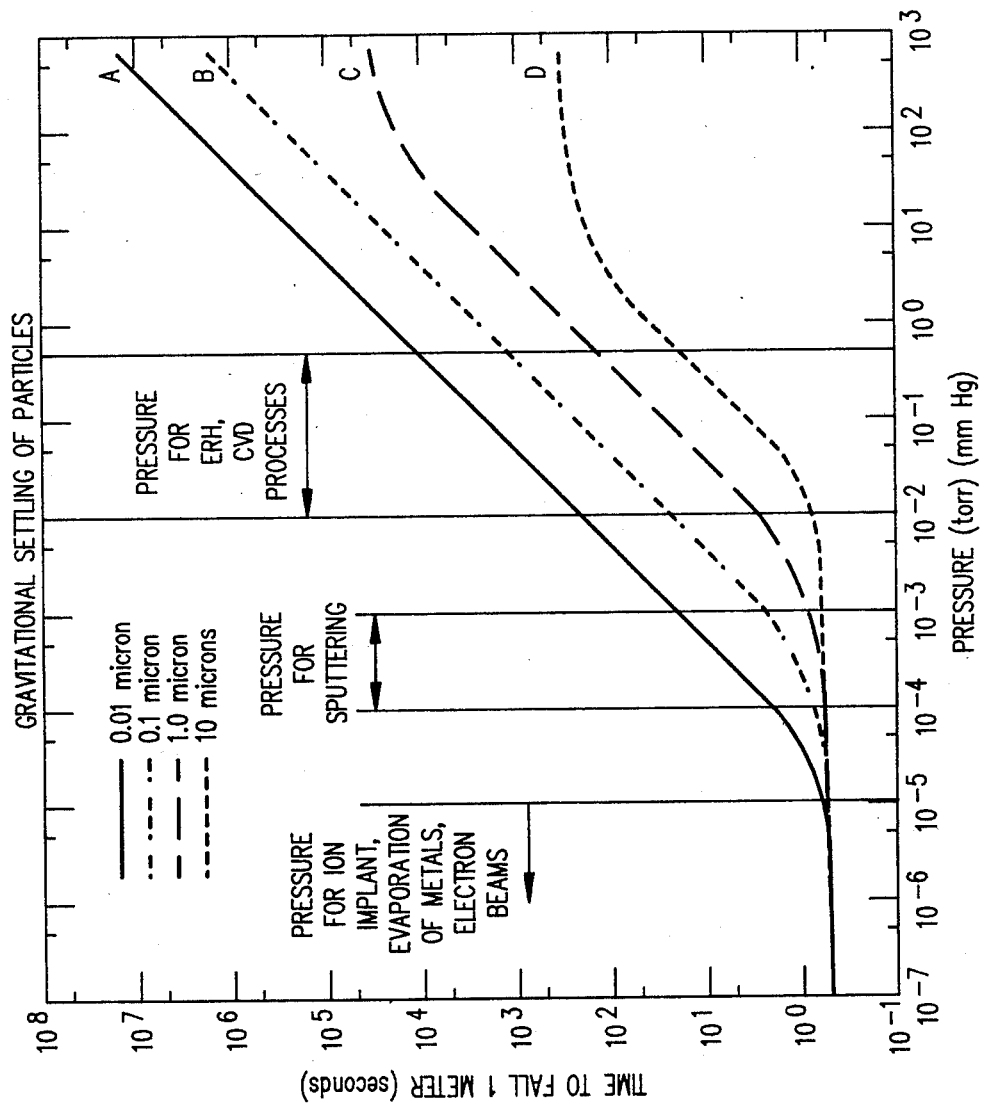
FIG. 2 is a series of waveforms A–D representing the gravitational settling of particles for different size particles over a defined pressure range.

The method by which particles are sampled is a function of the vacuum chamber pressure. FIG. 2 illustrates the time it takes to fall 1 meter for various size particles as a function of pressure. FIG. 2 shows the pressures at which various semiconductor production processes operate. For processes such as sputtering, ion implantation, metal evaporation and electron beam lithography, the pressures are so low that even very small particles fall very rapidly. For these systems, the sample probe 12 is substantially vertical and the saturation column 5 is located directly underneath. Certain processes such as plasma etching and chemical vapor deposition (CVD) operate at higher pressures, where particles in the size range of 0.01 to 0.1 microns in diameter fall very slowly, and are borne by the gas flow. In these cases, the sample probe need not be vertical, and the line connecting it to the saturation column 5 can be bent without serious effect on the DPNC performance.

A typical diffusion pump oil used for the DPNC is Fomblin 425/9. The oil has a very low vapor pressure, about 5E-8 Torr at 25 degrees C. and it has a very high molecular weight of 2600. Also, it is inert to halides such as fluorine and chlorine, which are often used in semiconductor processes. Because of the high molecular weight of this oil, it will not undergo homogeneous nucleation.

While homogeneous nucleation can occur with the process employed in accordance with this invention, it is most unlikely. The Kelvin equation gives the pressure at which homogeneous nucleation can occur as $$p = p_s \exp \frac{4\gamma M}{\rho RTd^*}$$

where $p_s$ is the vapor pressure, $\gamma$ is the surface tension of the oil, and M, $\rho$, and $d^*$ are the molecular weight, density and molecular size of the oil molecules respectively. R is the ideal gas constant and T the temperature. For Fomblin 425/9, the exponent of this equation is almost 200, so homogeneous nucleation is unlikely to occur.

The rate at which the oil droplets, which have formed around particles to be detected, grow is given by $$\frac{\delta d}{\delta t} = \frac{2Mp}{\rho N_a \sqrt{2\pi mkT}}$$

where p is the background pressure, $N_a$ is Avagadro's number, m is the mass of a vapor molecule, and k is Boltzmann's constant. For a background pressure of 50 milliTorr, this rate is about 100 microns per second. For a particle to grow to an easily detectable size of about 10 microns, it must be in the system for only 0.1 second. Under the assumption that the droplets quickly grows large enough to fall under the influence of gravity, it need fall only about 5 centimeters, reaching a velocity of 1 meter per second, to grow to a size of 10 microns. This computation provides the minimum height of the saturation column. However, it may be desirable to make the saturation column longer, say 20 to 30 cm, to allow oil vapors to adequately condense before reaching the optical system. A longer column prevents oil condensation on the windows, which if it occurred would have an adverse effect on optical performance.

There has been disclosed herein a novel system for detection of extremely small particles in a low pressure environment. The system affords the advantages of real-time detection of spurious particles and contaminants during the processing of semiconductor wafers.

It should be understood that the invention is not necessarily limited to the parameters, dimensions and materials specified herein but may be modified well within the scope of the invention.

What is claimed is:

1. A system for detecting extremely small particles in a low pressure environment comprising:
    a vapor column including an oil reservoir containing diffusion pump oil;
    a saturation column coupled to said vapor column and to said low pressure environment, said vapor column and saturation column being coupled to form a loop;
    means for heating and vaporizing said oil to form oil vapors that rise in said vapor column;

cooling means coupled to said saturation column for condensing and supersaturating and forming liquid droplets of said oil vapors thereby providing a pumping action in the saturation column so that no backflow of oil vapors into said low pressure environment occurs; and optical detection means disposed adjacent to said saturation column for detecting said droplets as they descend in said saturation column.

2. A system as in claim 1, including an oil return conduit connected between said saturation column and said oil reservoir for recycling the oil to be vaporized.

3. A system as in claim 1, including a vacuum pump coupled to said saturation column for maintaining a predetermined low pressure in said system.

4. A system as in claim 3, wherein said predetermined low pressure is less than 100 milliTorr.

5. A system as in claim 1, wherein said optical detection means comprises a laser and a lens for directing a collimated beam of light through said saturation column.

6. A system as in claim 5, including photodetection means located adjacent to said saturation column for receiving scattered light resulting from impingement of said beam on droplets with particles falling through said beam.

7. A system as in claim 6, including spaced windows formed in said saturation column for allowing passage of said beam to said photodetection means.

8. A system as in claim 1, including having a nozzle through which vaporized liquid is passed from the vapor column to the saturation column.

* * * * *